United States Patent
Wan et al.

(10) Patent No.: US 9,886,534 B2
(45) Date of Patent: Feb. 6, 2018

(54) SYSTEM AND METHOD FOR COLLISION AVOIDANCE IN MEDICAL SYSTEMS

(71) Applicant: Varian Medical Systems, Inc., Palo Alto, CA (US)

(72) Inventors: Hong Wan, Sammamish, WA (US); Raymond Kraft, Seattle, WA (US); Sun-Kai Lin, Seattle, WA (US); Stephen C. Phillips, Woodinville, WA (US); Anthony Harrington, Woodinville, WA (US); Hassan Mostafavi, Los Altos, CA (US); Alexander Sloutsky, Burlingame, CA (US); Andrew G. Jeung, Mountain View, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 59 days.

(21) Appl. No.: 15/014,813

(22) Filed: Feb. 3, 2016

(65) Prior Publication Data

US 2017/0220709 A1 Aug. 3, 2017

(51) Int. Cl.
*A61N 5/10* (2006.01)
*G06F 17/50* (2006.01)

(52) U.S. Cl.
CPC ....... *G06F 17/5009* (2013.01); *A61N 5/1048* (2013.01)

(58) Field of Classification Search
CPC .. G06T 7/50; G06T 7/521; G06T 7/70; G06T 7/75; G06T 17/00; A61B 6/102;

(Continued)

(56) References Cited

U.S. PATENT DOCUMENTS

| 3,720,817 A | 3/1973 | Dinwiddie | ......... A61B 19/2203 |
| 6,272,368 B1 | 8/2001 | Alexandrescu | ............... 600/407 |

(Continued)

FOREIGN PATENT DOCUMENTS

| CN | 200984237 Y | 12/2007 |
| DE | 10 2008 046 345 B4 | 7/2010 |

(Continued)

OTHER PUBLICATIONS

International Search Report and Written Opinion dated Apr. 28, 2017 for corresponding PCT Patent Application No. PCT/US17/16217, 16 pages.

*Primary Examiner* — Andrew W Johns
(74) *Attorney, Agent, or Firm* — Vista IP Law Group, LLP

(57) ABSTRACT

A method of detecting a possible collision in a medical procedure that involves a medical system, includes: obtaining an image of a patient that is supported on a patient support; determining a first model using a processing unit based at least in part on the image, at least a part of the first model representing a surface of the patient; determining a second model using the processing unit, the second model representing a first component of the medical system; virtually moving the first model, the second model, or both, using a collision prediction mechanism to simulate a movement of the first component of the medical system to determine whether there is a possible collision between the first component and the patient; and generating an output to indicate the possible collision or an absence of the possible collision.

32 Claims, 9 Drawing Sheets

(58) Field of Classification Search
CPC .............. A61B 34/10; A61B 2034/101; A61B 2034/105; A61B 2034/107; A61B 34/20; A61B 2034/2055; A61B 2034/2057; A61B 2034/2065; A61N 5/103; A61N 5/1048; G05B 19/4061; G05B 2219/49143

See application file for complete search history.

(56) References Cited

U.S. PATENT DOCUMENTS

| | | |
|---|---|---|
| 6,504,899 B2 | 1/2003 | Pugachev et al. .............. 378/65 |
| 6,735,277 B2 | 5/2004 | McNutt et al. ................. 378/65 |
| 7,245,698 B2 | 7/2007 | Pang et al. ..................... 378/65 |
| 7,268,358 B2 | 9/2007 | Ma et al. .................... 250/492.3 |
| 7,529,339 B2 | 5/2009 | Goldman et al. .............. 378/65 |
| 7,773,723 B2 | 8/2010 | Nord et al. ..................... 378/65 |
| 7,835,494 B2 | 11/2010 | Nord et al. ..................... 378/65 |
| 8,175,892 B2 | 5/2012 | Kapoor et al. ................... 705/2 |
| 8,986,186 B2 | 3/2015 | Zhang et al. ........... A61N 5/103 |
| 9,211,423 B2 | 12/2015 | Gross et al. .......... A61N 5/1049 |
| 2002/0154269 A1 | 10/2002 | Liu et al. ...................... 351/206 |
| 2004/0042583 A1 | 3/2004 | Wackerle et al. ............... 378/65 |
| 2012/0271094 A1 | 10/2012 | Fuller ............................... 600/1 |
| 2013/0083894 A1 | 4/2013 | Niebler et al. ................. 378/62 |
| 2013/0142310 A1 | 6/2013 | Fahimian et al. ...... A61N 5/103 |
| 2014/0240467 A1 | 8/2014 | Petyushko et al. .... H04N 5/232 |
| 2014/0376790 A1 | 12/2014 | Mostafavi ............ G06T 7/0044 |
| 2015/0005785 A1 | 1/2015 | Olson ...................... 235/151.11 |
| 2015/0035942 A1 | 2/2015 | Hampton et al. ..... G06T 19/006 |
| 2015/0045604 A1 | 2/2015 | Sawkey et al. ....... A61N 5/1068 |
| 2015/0208999 A1 | 7/2015 | Steinfeld et al. ....... B61B 6/547 |
| 2015/0324967 A1 | 11/2015 | Newell et al. .......... G06T 7/004 |

FOREIGN PATENT DOCUMENTS

| | | |
|---|---|---|
| DE | 10 2012 203 767 A1 | 7/2013 |
| JP | 2014-128352 A | 7/2014 |
| WO | WO 2011/153639 A2 | 12/2011 |
| WO | WO 2015/017630 A1 | 2/2015 |
| WO | WO 2015/017639 A1 | 2/2015 |
| WO | WO 2016/014422 A1 | 1/2016 |

SYSTEM AND METHOD FOR COLLISION AVOIDANCE IN MEDICAL SYSTEMS

FIELD

The field of the application relates to systems and methods for detecting a possible collision between an object and a patient during a medical procedure, wherein the object may be a part of a medical device.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. During a radiation therapy, a radiation source may be rotated around a patient to deliver radiation from different angles at target region inside the patient. The radiation source may be mounted on an arm or a ring gantry. In certain radiation therapy, the patient support supporting the patient may also be moved. Despite careful treatment planning, during a medical procedure, a collision may occur between a moving part of a medical device and a patient. For example, the gantry of the radiation machine and the patient may possibly collide during radiation therapy. As the dose delivery plans become more complex, the combination of a rotating gantry during treatment and couch movement for non-coplanar beams delivery increases the chance of collisions.

While gantry mounted laser systems and room mounted scanners have been used to detect possible collisions, these methods have disadvantages. While a gantry mounted laser system has the ability to detect when a plane defined by laser scanning is intersected by an intruding object, it does not work in many situations where the couch is rotated.

Applicant of the subject application has determined that it may be desirable to develop a new collision avoidance system and method.

SUMMARY

An apparatus for detecting a possible collision in a medical procedure, includes: a camera for providing an image of a patient that is supported on a patient support; and a processing unit configured for: determining a first model based at least in part on the image, at least a part of the first model representing a surface of the patient, and determining a second model, the second model representing a first component of the medical system; and a collision prediction mechanism configured for virtually moving the second model to simulate a movement of the first component of the medical system to determine whether there is a possible collision between the first component and the patient; wherein the collision prediction mechanism is also configured for generating an output to indicate the possible collision or an absence of the possible collision.

Optionally, the processing unit is also configured for determining a third model representing the patient support.

Optionally, the collision prediction mechanism is further configured for virtually moving the first model and the third model as a single unit.

Optionally, the first model includes a modeling of at least a part of the patient support.

Optionally, the collision prediction mechanism is further configured for virtually moving the first model to simulate a movement of the patient due to a movement of the patient support.

Optionally, the processing unit is configured for determining the first model in response to a movement of the patient.

Optionally, the processing unit is configured for determining the first model after the patient is set up for a treatment procedure.

Optionally, the processing unit is configured for determining the first model in response to a user entering a user input via a user interface.

Optionally, the apparatus further includes a graphical output interface for providing a graphic indicating a movement trajectory of the second model. In some cases, the first model may be undergoing motion that is coordinated with the second model. In such cases, the graphic may allow a user to view both models.

Optionally, the apparatus further includes a graphical output interface for providing a video indicating the virtual movement of the second model.

Optionally, the image comprises a depth image of the patient, and wherein the processing unit is configured for, in a process to determine the first model: identifying a portion in the depth image that corresponds with the surface of the patient; and using the identified portion in the depth image to create the first model.

Optionally, the processing unit is configured for, in a process to determine the first model: identifying a portion in another depth image that corresponds with another surface of the patient; and combining the portion from the depth image and the portion in the other depth image.

Optionally, the processing unit is configured for extracting a first set of points from the identified portion in the depth image.

Optionally, the processing unit is configured for, in a process to determine the first model: identifying a portion in another depth image that corresponds with another surface of the patient; extracting a second set of points from the identified portion in the other depth image; and determining a third set of points representing a protected surface associated with the patient using the first set of points and the second set of points.

Optionally, the third set of points includes at least some of the first set of points, and at least some of the second set of points.

Optionally, the protected surface represented by the third set of points is away from the surface of the patient, and wherein the third set of points are away from at least some of the first set of points, and are away from at least some of the second set of points.

Optionally, the processing unit is configured for, in a process to determine the first model, determining a protected surface that is away from the surface of the patient.

Optionally, the medical system comprises a radiation treatment system.

Optionally, the first component comprises a gantry, a radiation source, a portal imager, or a kV imager.

Optionally, the image comprises a depth image, and wherein the processing unit is further configured for removing stray points from the depth image.

Optionally, the collision prediction mechanism is configured for virtually moving the second model by executing a treatment plan virtually.

Optionally, the apparatus further includes a motion detection device configured to detect a motion of the patient; wherein the collision prediction mechanism is configured to, after the motion is detected, determine a position of the first component of the medical system.

Optionally, the collision prediction mechanism is configured for virtually moving the second model after the position of the first component of the medical system is determined.

Optionally, the processing unit is further configured for: determining a third model representing a second component of the medical system; and virtually moving the third model to simulate a movement of the second component.

Optionally, the collision prediction mechanism is a part of the processing unit.

Optionally, the camera is configured to generate the image based on time-of-flight technique, stereoscopic technique, structured light, or ultrasound.

Optionally, the apparatus further includes an optical device for providing infrared illumination or pattern projection for enhancing the stereoscopic technique.

Optionally, the depth sensing camera is configured to generate the image using ultrasound.

Optionally, the apparatus further includes an additional depth measuring camera.

Optionally, the image comprises a depth image, and wherein the processing unit is configured to obtain a visible image of the patient.

Optionally, the processing unit is configured to output both the visible image and the depth image for display on a screen.

A method of detecting a possible collision in a medical procedure that involves a medical system, includes: obtaining an image of a patient that is supported on a patient support; determining a first model using a processing unit based at least in part on the image, at least a part of the first model representing a surface of the patient; determining a second model using the processing unit, the second model representing a first component of the medical system; virtually moving the second model using a collision prediction mechanism to simulate a movement of the first component of the medical system to determine whether there is a possible collision between the first component and the patient; and generating an output to indicate the possible collision or an absence of the possible collision.

Optionally, the method further includes determining a third model representing the patient support.

Optionally, the method further includes virtually moving the first model and the third model as a single unit.

Optionally, the first model includes a modeling of at least a part of the patient support.

Optionally, the method further includes virtually moving the first model to simulate a movement of the patient due to a movement of the patient support.

Optionally, the act of determining the first model is performed in response to a movement of the patient.

Optionally, the act of determining the first model is performed after the patient is set up for a treatment procedure.

Optionally, the act of determining the first model is performed in response to a user entering a user input via a user interface.

Optionally, the method further includes displaying a graphic indicating a movement trajectory of the second model.

Optionally, the method further includes displaying a video indicating the virtual movement of the second model.

Optionally, the image comprises a depth image of the patient, and wherein the act of determining the first model comprises: identifying a portion in the depth image that corresponds with the surface of the patient; and using the identified portion in the depth image to create the first model.

Optionally, the act of determining the first model further comprises: identifying a portion in another depth image that corresponds with another surface of the patient; and combining the portion from the depth image and the portion in the other depth image.

Optionally, the act of determining the first model further comprises extracting a first set of points from the identified portion in the depth image.

Optionally, the act of determining the first model further comprises: identifying a portion in another depth image that corresponds with another surface of the patient; extracting a second set of points from the identified portion in the other depth image; and determining a third set of points representing a protected surface associated with the patient using the first set of points and the second set of points.

Optionally, the third set of points includes at least some of the first set of points, and at least some of the second set of points.

Optionally, the protected surface represented by the third set of points is away from the surface of the patient, and wherein the third set of points are away from at least some of the first set of points, and are away from at least some of the second set of points.

Optionally, the act of determining the first model further comprises determining a protected surface that is away from the surface of the patient.

Optionally, the medical system comprises a radiation treatment system.

Optionally, the first component comprises a gantry, a radiation source, a portal imager, or a kV imager.

Optionally, the image comprises a depth image, and wherein the method further comprises removing stray points from the depth image.

Optionally, the act of virtually moving the second model is performed by executing a treatment plan virtually.

Optionally, the method further includes: detecting a motion of the patient; and after the motion is detected, determining a position of the first component of the medical system.

Optionally, the act of virtually moving the second model is performed after the position of the first component of the medical system is determined.

Optionally, the method further includes: determining a third model representing a second component of the medical system; and virtually moving the third model to simulate a movement of the second component.

Optionally, the collision prediction mechanism is a part of the processing unit.

A product includes a non-transitory medium storing a set of instructions, an execution of which by a processing unit causes a method for detecting a possible collision in a medical procedure to be performed, the method comprising: obtaining an image of a patient that is supported on a patient support; determining a first model using the processing unit based at least in part on the image, at least a part of the first model representing a surface of the patient; determining a second model using the processing unit, the second model representing a first component of a medical system; virtually moving the second model using a collision prediction mechanism to simulate a movement of the first component of the medical system to determine whether there is a possible collision between the first component and the patient; and generating an output to indicate the possible collision or an absence of the possible collision.

Optionally, the method further comprises determining a third model representing the patient support.

Optionally, the method further comprises virtually moving the first model and the third model as a single unit.

Optionally, the first model includes a modeling of at least a part of the patient support.

Optionally, the method further comprises virtually moving the first model to simulate a movement of the patient due to a movement of the patient support.

Optionally, the act of determining the first model is performed in response to a movement of the patient.

Optionally, the act of determining the first model is performed after the patient is set up for a treatment procedure.

Optionally, the act of determining the first model is performed in response to a user entering a user input via a user interface.

Optionally, the method further comprises displaying a graphic indicating a movement trajectory of the second model.

Optionally, the method further comprises displaying a video indicating the virtual movement of the second model.

Optionally, the image comprises a depth image of the patient, and wherein the act of determining the first model comprises: identifying a portion in the depth image that corresponds with the surface of the patient; and using the identified portion in the depth image to create the first model.

Optionally, the act of determining the first model further comprises: identifying a portion in another depth image that corresponds with another surface of the patient; and combining the portion from the depth image and the portion in the other depth image.

Optionally, the act of determining the first model further comprises extracting a first set of points from the identified portion in the depth image.

Optionally, the act of determining the first model further comprises: identifying a portion in another depth image that corresponds with another surface of the patient; extracting a second set of points from the identified portion in the other depth image; and determining a third set of points representing a protected surface associated with the patient using the first set of points and the second set of points.

Optionally, the third set of points includes at least some of the first set of points, and at least some of the second set of points.

Optionally, the protected surface represented by the third set of points is away from the surface of the patient, and wherein the third set of points are away from at least some of the first set of points, and are away from at least some of the second set of points.

Optionally, the act of determining the first model further comprises determining a protected surface that is away from the surface of the patient.

Optionally, the medical system comprises a radiation treatment system.

Optionally, the first component comprises a gantry, a radiation source, a portal imager, or a kV imager.

Optionally, the image comprises a depth image, and wherein the method further comprises removing stray points from the depth image.

Optionally, the act of virtually moving the second model is performed by executing a treatment plan virtually.

Optionally, the method further comprises: detecting a motion of the patient; and after the motion is detected, determining a position of the first component of the medical system.

Optionally, the act of virtually moving the second model is performed after the position of the first component of the medical system is determined.

Optionally, the method further comprises: determining a third model representing a second component of the medical system; and virtually moving the third model to simulate a movement of the second component.

Optionally, the collision prediction mechanism is a part of the processing unit.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited features, other advantages, and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
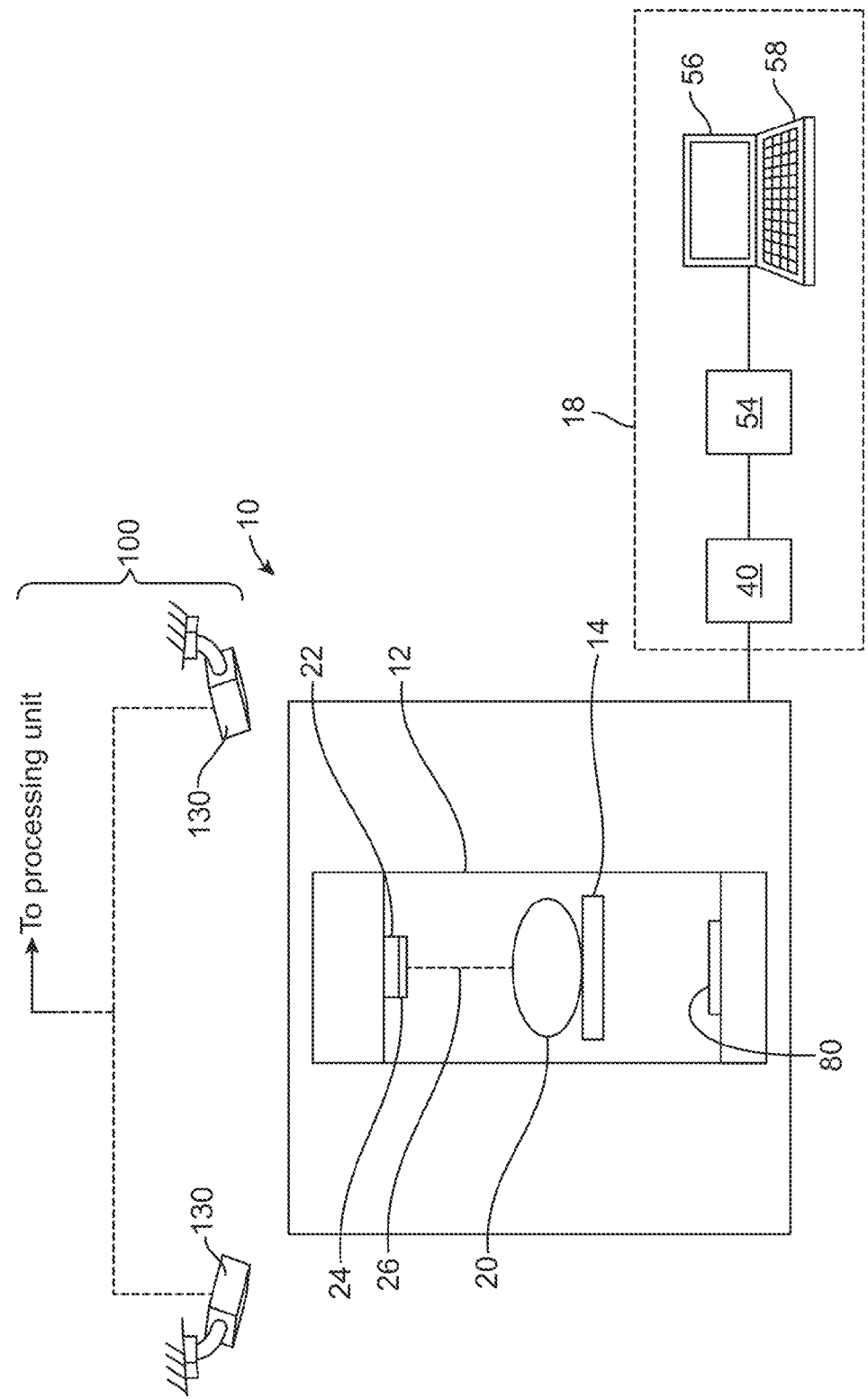
FIG. 1 illustrates a radiation treatment system configured for detecting possible collision between a moving part of a medical device and a patient during a medical procedure in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation treatment system 10. The system 10 includes an arm gantry 12, a patient support 14 for supporting a patient 20, and a control system 18 for controlling an operation of the gantry 12 and delivery of radiation. The system 10 also includes a radiation source 22 that projects a beam 26 of radiation towards the patient 20 while the patient 20 is supported on support 14, and a collimator system 24 for changing a cross sectional shape of the radiation beam 26. The radiation source 22 may be configured to generate a cone beam, a fan beam, or other types of radiation beams in different embodiments. Also, in other embodiments, the source 22 may be configured to generate a proton beam, electron beam, or neutron beam, as a form of radiation for treatment purpose. Also, in other embodiments, the system 10 may have other form and/or configuration. For example, in other embodiments, instead of an arm gantry 12, the system 10 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may be used to obtain images. In such cases, in order to obtain imaging using treatment energies, the imager 80 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 22 is able to generate X-ray radiation at a plurality of photon energy levels within a range anywhere between approximately 10 keV and approximately 20 MeV. In further embodiments, the radiation source 22 can be a diagnostic radiation source. In such cases, the system 10 may be a diagnostic system with one or more moving parts. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. Although the control 40 is shown as a separate component from the gantry 12 and the processing unit 54, in alternative embodiments, the control 40 can be a part of the gantry 12 or the processing unit 54.

In some embodiments, the system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

Figure 2:
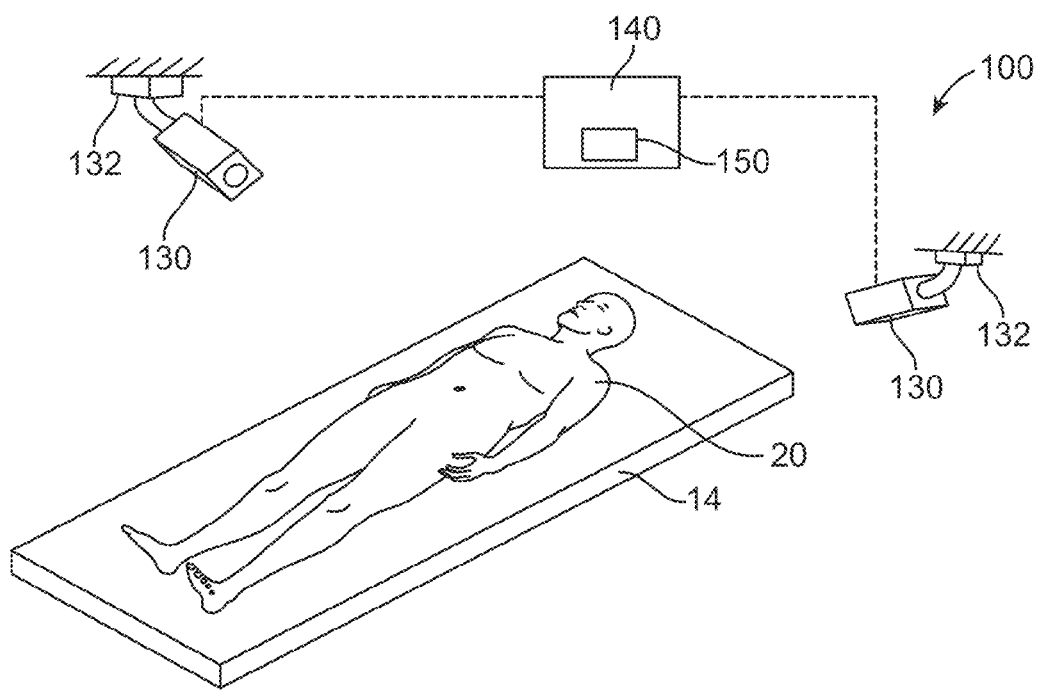
FIG. 2 illustrates a system for determining whether there is a possible collision between a patient and an object.

As shown in FIGS. 1 and 2, the medical system 10 also includes a collision prediction system 100, which includes two depth measuring cameras 130, and a securing mechanism 132 for securing the depth measuring camera 130 relative to an object (e.g., a wall, a ceiling, a floor, a stand, or any of the components in the system 10, such as the gantry 12, the patient support 14, etc.).

Each depth sensing camera 130 is configured to sense depths and to generate signals representing the depths. The depth sensing camera 130 is configured to provide a two-dimensional image, wherein each pixel in the two-dimensional image represents a distance from a reference location (e.g., from the camera 130). In some embodiments, the depth sensing camera 130 may use structured light for depth measurement (e.g., a Kinect camera). For example, a projector may be used to project a known pattern (structured light), e.g., grids, horizontal bars, etc., on to a scene, and the way the pattern deforms when striking the surface may allow depth and surface information of the object in the scene be determined. In other embodiments, the depth sensing camera 130 may use time-of-flight method for depth measurement (e.g., Mesa SR4000, or the new Microsoft Kinect2 camera). In further embodiments, the depth sensing camera 130 may be any device that is capable of sensing depth using any known techniques. It should be noted that the term "camera", as used in this specification, may be any device, and should not be limited to a device that provides "image" signals. For example, in some embodiments, the depth sensing camera 130 may be configured to provide depth signals, which may or may not be considered image signals, regardless of whether such depth signals are displayed in image form or not. A depth signal may be any signal indicating a depth or distance, or any signal from with a depth or distance may be derived. By means of non-limiting examples, the signal may be an infrared signal, an ultrasound signal, etc. In some embodiments, the dimensions of the depth sensing camera 130 may be small enough to be non-intrusive to the treatment process when mounted during use. For example, in some embodiments, the camera 130 may have a dimension of 11 inch×2.5 inch×1.5 inch. In other embodiments, the camera 130 may have other dimensions, such as those larger or smaller than the example provided above, as long as the use of the camera 130 does not interfere with the treatment procedure.

Also, in further embodiments, the camera 130 may be any of other types of depth camera. For example, the camera 130 may be a stereoscopic camera with/without illumination, a stereoscopic camera with a projected pattern, or a depth camera using structured light. Also, in some embodiments, the collision prediction system 100 may include multiple (e.g., two, three, etc.) stereoscopic cameras. In one implementation, each stereoscopic camera may be an alignRT camera from VisionRT.

Figure 3:
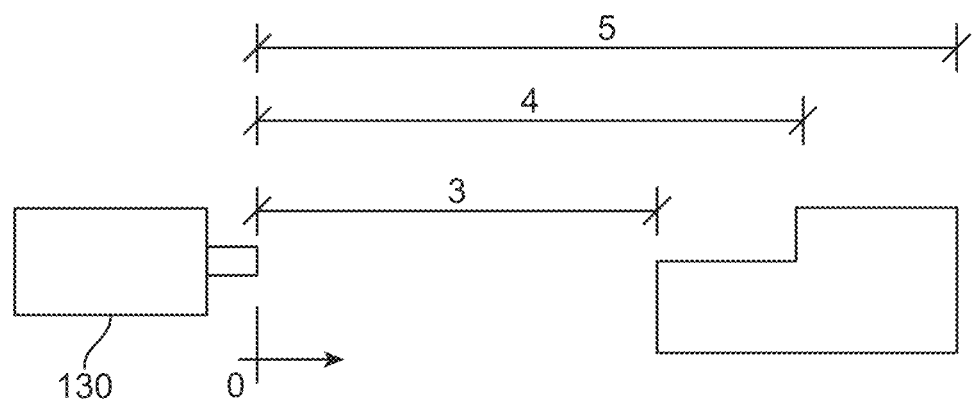
FIG. 3 illustrates a time-of-flight technique used by a depth sensing camera.

Because the depth sensing camera 130 is configured to sense depth, the two-dimensional image it produces has an array of pixel values that indicate respective distances between the camera 130 (i.e., the sensors in the camera 130) and different objects (or different parts of an object). For example, as shown in FIG. 3, an arbitrary origin may be set to be at the camera, and so an object that is further away from the camera 130 will have a corresponding sensed depth by the camera 130 that has a higher value than another object that is closer to the camera 130. Thus, a pixel with a smaller value indicates that the sensed object is closer to the depth sensing camera 130 compared to a pixel that has a larger value.

Also, in some embodiments, the depth sensing camera 130 may be infrared-based, in which cases, the depth may be sensed by the camera 130 using infrared. In some embodiments, such depth sensing camera 130 may be configured to output infrared video images from which depth images are formed. In some embodiments, these infrared video images may have exactly the same field of view as the depth images. Thus, the infrared video images may be used together with the depth images to determine whether there is a possible collision.

Furthermore, in some embodiments, the depth sensing camera 130 may include an infrared emitter, a color sensor, and an infrared depth sensor. The infrared depth sensor is configured to sense depth based on infrared signals output by the infrared emitter. The color sensor is configured to sense visible image.

In some embodiments, the depth sensing camera 130 may have a detection (or frame) rate of 30 per second or higher. In other embodiments, the detection/frame rate may be less than 30 per second.

In some embodiments, the securing mechanism 132 may be configured to secure the depth measuring camera 130 to a part of the medical system 10, or to a structure that is not a part of the medical system 10. The securing mechanism 132 may be a clamp for grasping an object, a screw for insertion into a screw slot located in an object to which the depth measuring camera 130 is to be secured against, a snap-and-fit type connector, a hook-and-loop type connector, or any of other types of securing mechanism. In still further embodiments, the securing mechanism 132 is not required, and the collision prediction system 100 does not include the securing mechanism 132. For example, in other embodiments, the support 134 may be a base, and the base may be placed on a flat surface that supports the depth sensing camera 130 during use.

Also, in some embodiments, the depth sensing camera 130 may be moveably coupled to the securing mechanism 132. For example, the depth sensing camera 130 may be coupled to the securing mechanism 132 via a support (not shown). The support may be a post, a bracket, a beam, an arm, etc., for supporting the depth sensing camera 130. The securing mechanism 132 may be located at the support. Also, in some embodiments, the support may optionally have one or more moveable parts to allow a position and/or an orientation of the depth sensing camera 130 to be adjusted. In some embodiments, a first part of the support may be movable relative to a second part of the support in order to adjust the camera position (e.g., in a linear direction and/or in a rotation). For example, the first part and the second part of the support may be implemented using a telescopic arm. As another example, the first part of the support may be rotatably coupled to the second part of the support via a hinge or a ball socket. In further embodiments, the support may be a base with a tilt motor, which allows the camera 130 to be tilted in one, two, or three, degrees of movement relative to the base. In other embodiments, the support is not needed, and the collision prediction system 1000 may not include the support. In further embodiments, the camera 130 may be mounted on a motorized support.

Although two depth cameras 130 are shown in the illustrated embodiments, in other cases, the collision prediction system 100 may include only a single depth sensing camera 130, or more than three depth sensing cameras 130. For example, in other embodiments, there may be one or more additional depth sensing cameras 130 pointing at different parts of the treatment system 10.

As shown in FIG. 2, the collision prediction system 100 also includes a processing unit 140 communicatively coupled to the depth sensing camera 130. The processing unit 140 is configured to process signals transmitted from the depth sensing camera 130, and to determine whether there is a possible collision between the patient and an object based on the signals. In some embodiments, the processing unit 140 may be a processor, such as an ASIC processor, a FPGA processor, a general purpose processor, or any of other types of processor. Also, the processing unit 140 may include hardware, software, or combination of both. Also, in some embodiments, the processing unit 140 may be the same as the processing unit 54, or a component of the processing unit 54. In other embodiments, the processing unit 140 may be considered to be a part of the treatment system 10, and not a part of the collision prediction system 100.

In the illustrated embodiments, the processing unit 140 is configured for determining a first model based at least in part on the image, at least a part of the first model representing a surface of the patient. The processing unit 140 is also configured for determining a second model, the second model representing a first component of the medical system. It should be noted that as used in this specification, the term "component" may refer to any portion of a medical system, which portion may be a device or a part of a device. For example, with respect to the patient support 14, the component may be the patient support 14 itself, an individual part (such as a plate forming the support surface of the patient support 14), or a portion of the individual part of the patient support 14, such as a surface that is a subset of all of the surfaces of an individual part of the patient support 14. Also, the collision prediction system 100 includes a collision prediction mechanism 150 configured for virtually moving the first model, the second model, or both, to simulate a movement of the first component of the medical system to determine whether there is a possible collision between the first component and the patient. Also, the collision prediction mechanism 150 may be configured for generating an output to indicate the possible collision or an absence of the possible collision. The collision prediction mechanism 150 may be implemented as a module in the processing unit 140 (as shown in the figure), or as a separate processing unit.

During use of the collision prediction system 100, the patient 20 is first positioned on the patient support 14 of the radiation treatment system 10. This may be performed during a treatment session after and/or during a patient setup procedure. The cameras 130 view the patient, and are then used to generate depth images. As used in this specification, the term "image" may refer to any group of data (e.g., depth values), which may or may not be displayed in image form. For example, the data may be stored in a non-transitory medium, and/or may be processed by the processing unit 140 without being displayed to a user for viewing. The depth images include information regarding a surface of the patient. In particular, the depth images will indicate a surface profile of the surface of the patient. As used in this specification, the term "surface" of the patient 20 is not limited to a skin surface of the patient 20, and may refer to other object(s) that is coupled to, or extends from, the patient. For example, the surface of the patient 20 may be the surface of a gown being worn by the patient 20, the surface of a cloth being worn by the patient 20, a blanket covering the patient 20, a towel covering the patient, a facemask, a goggle, a glasses, a breathing device, a catheter or a tube connected to the patient 20, etc.

Also, in some embodiments, a safety margin may be provided for the patient surface that is desired to be protected. In such cases, the surface of the patient may be a protected surface that is away from the actual patient's surface. For example, the protected surface may be defined as a surface that is 5 cm (or any of other values) away from, and surrounding, the actual patient's surface. Thus, the "surface" of the patient may refer to the actual surface of the patient 20, a surface of object(s) connected to or extending from the patient 20, or a surface (e.g., a virtual surface that is the protected surface) that is away from and surrounding the actual patient's surface.

The depth images provided by the cameras 130 may also include surface contours of other objects in the treatment room. For example, the depth images may include surface information regarding the patient support 14, the gantry 12, the collimator 24, the imager 80 (which may be a portal imager), and kV imager, which indicate the surface contours of these components.

After the depth images are generated, the cameras 130 transmit the depth images to the processing unit 140 for processing. The processing unit 140 performs image processing to determine surfaces that are desired to be protected during a treatment session performed by the treatment system 10. In some embodiments, the processing unit 140 may include a stray point removal module configured to detect and remove stray points in the depth image. Stray points are pixel error or noise that does not represent any part of an actual surface. Thus, removal of such stray points will reduce noise in the depth image and improve accuracy and quality of the surface detection. In one implementation, the stray point removal module is configured to detect a stray point by determining whether for a given pixel value, there is any adjacent pixel having a value that is within a certain range from the given pixel value. For example, if the depth image includes a pixel value of "50", the stray point removal module may be configured to determine if surrounding pixels (e.g., pixels within a 3×3, 4×4, etc. window or region of interest) has a depth value that is within 2 units from 50 (e.g., 50±2). If the number of pixels in the region of interest having pixel values within the given range exceeds a certain number (e.g., 3 or more), then the stray point removal module may determine that the pixel with the pixel value of "50" is a legitimate pixel that is a part of a surface. Otherwise, the stray point removal module may determine that the pixel with the pixel value of "50" is a stray point that is not a part of any surface, in which case, the stray point removal module may remove such pixel value by replacing the value with a value of an adjacent pixel.

Also, in some cases, the processing unit 140 may also include three-dimensional rendering algorithms for rendering surfaces in a way suitable for visual presentation. For example, the three dimensional rendering algorithm may down-sample, up-sample, perform surface meshing, etc.

In the illustrated embodiments, the processing unit 140 processes the depth images to identify surfaces that are desired to be protected. In some cases, this may be performed automatically. In other cases, a user may provide input to the processing unit 140 to identify the different surfaces that are desired to be protected during the treatment procedure. In one implementation, each camera 130 may have optical imaging capability (in addition to depth imaging), and may provide an optical image for display on a screen. The user may view the optical image together with the depth image, in a side-by-side configuration or an overlay configuration, and may then identify different surfaces. For example, the user may enter an input to identify a surface to be a surface of the gantry 12, an input to identify a surface of the patient 20, an input to identify a surface of the patient support 14, an input to identify a surface of the imager 80, an input to identify a surface of a kV imager, etc. In some cases, the user may also use a user interface to contour the surface of the patient and other part(s) of the treatment system.

Figure 4:
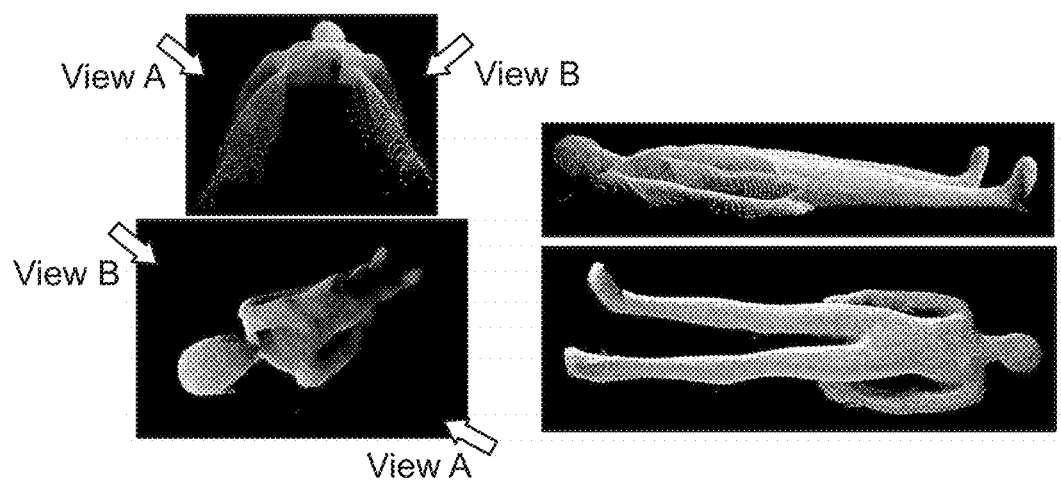
FIG. 4 illustrates an example of a model representing a surface of a patient.

In the illustrated example, the collision prediction system 100 includes two depth cameras 130 positioned to view opposite sides of the patient 20. In particular, there is a first depth camera 130 positioned to view the patient 20 from his/her right side, and a second depth camera 130 positioned to view the patient 20 from his/her left side. In another example, there may be a first camera 130 positioned to view the patient 20 from above his/her head towards a direction of the feet, and a second camera 130 positioned to view the patient 20 from below his/her feet towards a direction of the heard. Having two opposite cameras 130 is advantageous because it allows a substantially complete (e.g., 70% or greater, such as 80%, and more preferably 90%) surface of the patient 20 to be captured by the combination of the depth cameras 130. In some embodiments, the processing unit 140 may be configured to receive a first depth image from the first depth camera 130, and to receive a second depth image from the second depth camera 130. Because the relative position between the two depth cameras 130 is known, the processing unit 140 may use this positional information to perform coordinate transformation so that the surfaces of the patient 20 from the two depth images may be combined to form a continuous surface. FIG. 4 illustrates an example of surface points forming a surface model for the surface of the patient. The surface model is formed by combining a first surface model representing a right side of the patient 20 (viewed by a first camera 130—View A) with a second surface model representing a left side of the patient 20 (viewed by a second camera 130—View B). In some cases, the alignment of the two surface models may not be perfect, resulting in a combined model having a "double wall" at the connection area of the two surface models. The processing unit 140 may be configured to detect this "double wall" feature, and adjust the position of one or both of the surface models so that the boundaries of the two surface models for the patient can be aligned.

In further embodiments, the collision prediction system 100 includes more than two depth cameras 130 (e.g., three cameras 130, four cameras 130, etc.). In such cases, the surface model may be formed by combining point clouds from the different cameras 130.

Also, in some embodiments, the processing unit 140 may be configured to determine a protected surface from a point cloud of the entire field of view of a camera, or a merged multi-camera view based on expected and/or detected protected surface location and dimension. In some cases, a region of interest (e.g., a rectangular bounding box) may be employed by the processing unit 140 to detect protected surface location and dimension. For example, if the gantry 12 is expected to be at certain part of an image from the camera 130, then the processing unit 140 may be configured to search for a surface of the gantry 12 in a region of interest at that location in the image. In other cases, the processing unit 140 may be configured to identify surface(s) of interest by fitting of the actual point cloud or part of it to a geometrical model (parametric or numeric) that is known to represent the protected surface (or part of it) in order to determine the location and extent of the protected surface more intelligently. An example may be the patient support 14 that is part of the protected surface and known to be flat with a known dimension (which can then be represented by a parametric model). Another example may be a portion of the patient body whose model (in a numeric form) may come from pretreatment imaging. A further example may be the gantry head or a portion of it that could fall into the scene of the camera capture, and whose 3D model is known and can be built in a numeric form. Detection and delineation of the portions of the protected surface that correspond to those models through model fitting and matching (e.g., pattern matching) may provide the processing unit 140 with certain information that allows the processing unit 140 to either detect the actual location and extent of the protected surface, or to identify those regions that do not belong to it (such as the gantry head). In either case, the processing unit 140 can determine the protected surface more accurately and with fewer clutters.

In addition, in some embodiments, a two-dimensional optical image may be obtained to assist the processing unit 140 in identifying surfaces of interest. For example, a correspondence between the two-dimensional optical image and the 3D point cloud data from the depth image may be established on a pixel-by-pixel basis. Also, information (such as grayscale, color, edge, shape, dimension, etc., or a combination of these properties) not present in the 3D point cloud information may be obtained from the two-dimensional optical image, and may be used by the processing unit 140 to identify surfaces (e.g., surface of the patient support 14, etc.).

After different surfaces that are desired to be protected during the treatment procedure are identified, the surfaces may then be processed by the processing unit 140 to determine different models representing the different objects having the identified surfaces. In some cases, the surfaces themselves may be the models representing the different respective objects involved in the treatment procedure. For example, the coordinates of the pixel points forming the identified surface of the patient 20 may form a first model representing the surface of the patient 20. As another example, the coordinates of the pixel points forming the identified surface of the gantry 12 may form a second model representing the gantry 12. Similarly, the coordinates of the pixel points forming the identified surface of the patient support 14 may form a third model representing the patient support 14. In addition, the coordinates of the pixel points forming the identified surface of the imager 80 may form a fourth model representing the imager 80. Also, if the treatment system 10 includes a kV imager, the coordinates of the pixel points forming the identified surface of the kV imager may form a fifth model representing the kV imager. In some embodiments, the models of the various objects may be stored in a non-transitory medium for later use. Also, in some embodiments, the models of the various objects may be displayed on a screen for presentation to a user.

In other embodiments, models of the machine components do not need to come from pixel points. For example, in other embodiments, models of the machine components may be based on libraries of known shapes of these components. In some embodiments, the models of the machine components may be determined based on information (e.g., spec, CAD figures, etc.) obtained from manufacturer, or from a server that stores dimensional information and movement information regarding the components.

In other cases, each model of the object may include a protected surface that is away from the surface points provided from the depth camera(s) representing the actual surface of the object.

Figure 5A:
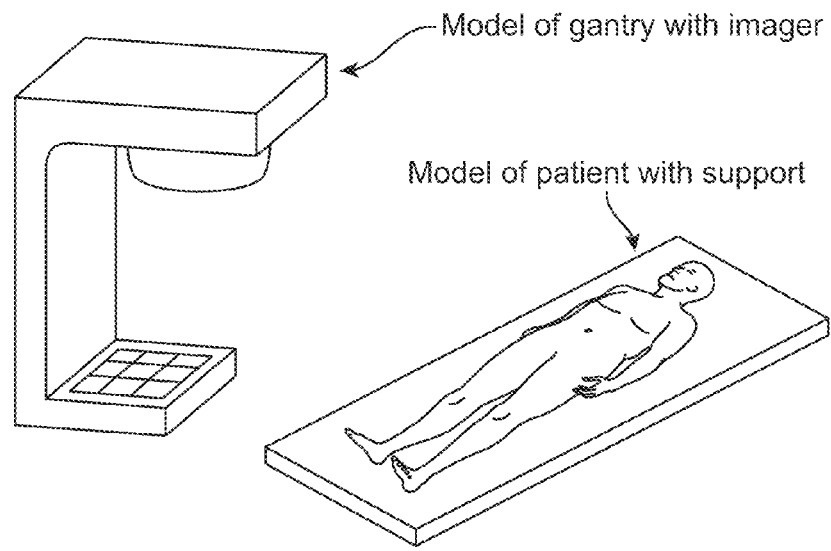
FIG. 5A illustrates different models representing different objects involved in a treatment procedure.

FIG. 5A illustrates an example in which the processing unit 140 determines two models of the objects involved in the treatment procedure. As shown in the figure, there is a first model representing a surface of the patient 20 on the support 14. There is also a second model representing a surface of the gantry 12 with imager 80. The models may represent the actual surfaces of the objects, or protected surfaces that are away from the actual surfaces of the objects.

In some embodiments, the models of the various objects may optionally include information regarding their respective positions and/or degrees of movements. For example, the model of the gantry 12 may include the position of the gantry 12 with respect to some coordinate system, such as a coordinate system of the treatment system 10, a coordinate system of the collision prediction system 100, or any of other arbitrary coordinate system. Alternatively, or additionally, the model of the gantry 12 may also include information regarding the degrees of movement for the gantry 12. For example, the model of the gantry 12 may include information regarding a rotational direction, axis of rotation, rotational rate, or any combination of the foregoing. Similarly, the model of the patient being supported on the patient support 14 may include information regarding a translational direction, axis of translation, translation rate, or any combination of the foregoing. For example, in the case in which the patient support 14 is configured to translate along X, Y, and Z axes, and to rotate about three orthogonal axes, the model may include these pieces of information.

Figure 5B:
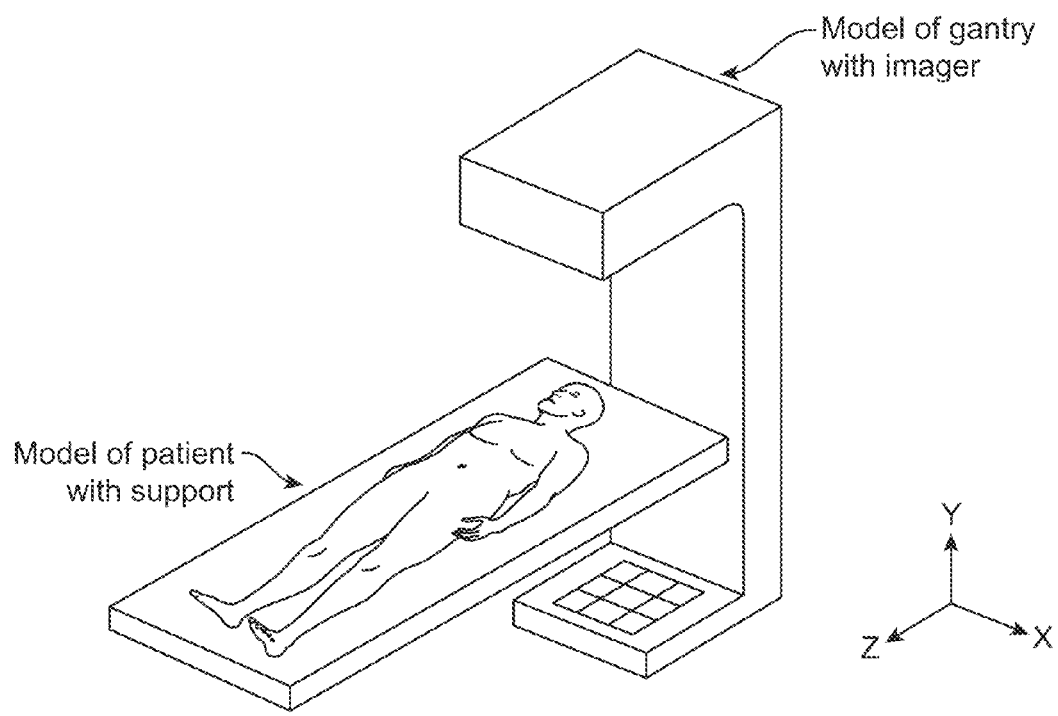
FIG. 5B illustrates the models of FIG. 5A being placed in a coordinate frame so that their relative positioning corresponding to that of the actual setup.

Also, in some embodiments, the collision prediction mechanism 150 may receive information regarding the current actual positions of the components of the treatment system 10. For example, a communication interface may be provided between the treatment system 10 and the collision prediction mechanism 150, which reads and passes positions of the components of the treatment system 10 to the collision prediction mechanism 150. The collision prediction mechanism 150 may also be configured to positionally register the models of the various objects in certain coordinate system, such as the coordinate system of the treatment system 10, based on the actual positions of the components of the treatment system 10. In particular, the collision prediction mechanism 150 may position (e.g., translate and/or rotate) the models of the various objects to match the real-world setup that corresponds with the time the surface profile of the patient is captured. FIG. 5B illustrates the examples of the models of FIG. 5A, particularly showing the relative positioning of the models after they have been positioned to match the real-word setup. As discussed, in some cases, the positions of the components can be included as parts of the models representing those components.

In some embodiments, the model fitting and pattern matching described previously may also be used to help fine-tune the placement of the models representing the different surfaces of the objects in a coordinate system. For example, if the 6 degree of freedom (DOF) parameters (i.e., x, y, z, pitch, roll, and yaw) of the patient support 14 as provided by the treatment system 10 is known, the processing unit 140 can place the protected surface precisely in the coordinate system (e.g., a treatment room coordinate system) used by the collision prediction system 100, as the position of the patient support 14 from the treatment system 10 is registered in the treatment room coordinate system. However, due to patient weight, the patient support 14 may undergo a certain deflection and pitch resulting in a similar movement of the protected surface at the patient support 14. In such case, adjusting the 6 DOF parameters associated with the patient support 14 may not be sufficient to match that movement, as the 6 DOF parameters are defined assuming the patient support 14 rotating around an ISO center but the couch deflection and pitch under the patient weight does not follow that assumption. In this case, detecting and delineating the surface of the patient support 14 would allow the processing unit 140 to more accurately place the protected surface in the collision model, and improve the performance of the collision prediction system.

Figure 5C:
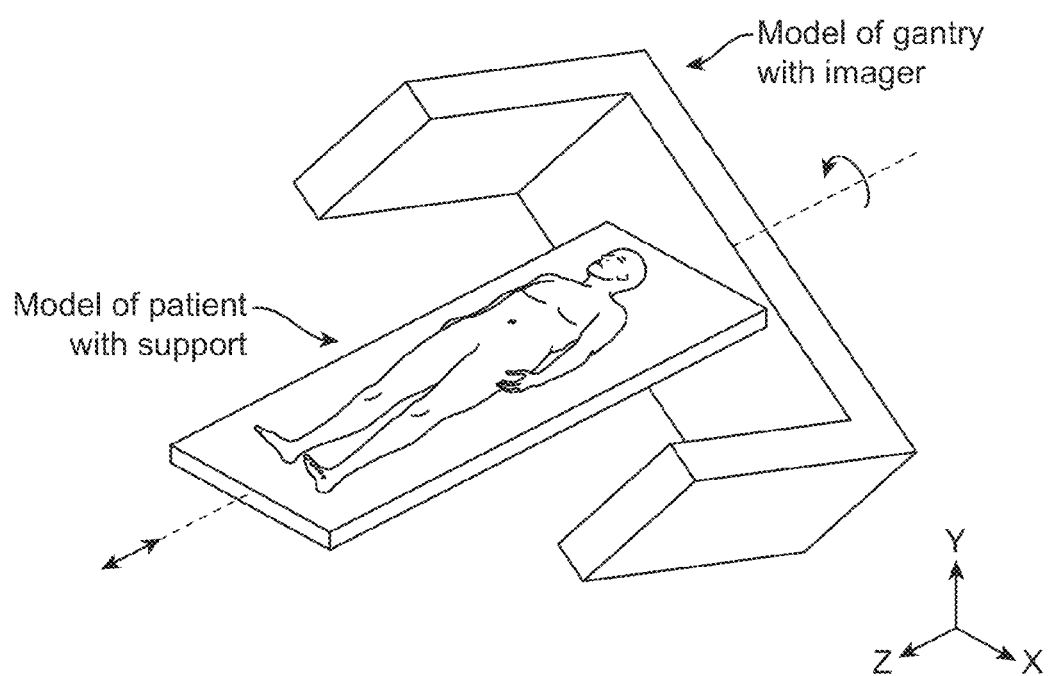
FIG. 5C illustrates examples of virtual movements of the models of FIG. 5B performed by a collision prediction mechanism.

After the models of the various objects involved have been determined by the processing unit 140, the processing unit 140 may then determine whether there is any possible collision between two or more objects that may happen if a treatment procedure is executed according to a treatment plan. In the illustrated embodiments, the collision prediction mechanism 150 in the processing unit 140 is configured to receive information regarding a treatment plan, and then virtually executes the treatment plan by virtually moving one or models to simulate movement of the object(s) represented by the model(s) based on the treatment plan information. For example, the treatment plan may prescribe that the patient support 14 supporting the patient be translated along the longitudinal axis of the patient support 14 from z-position of 5 cm to z-position of 6.6 cm, and then the gantry 12 be rotated from gantry angle 45° to gantry angle 49°. Based on these information, the collision prediction mechanism 150 then "virtually" (i.e., mathematically) moves the model representing the surface of the patient support 14 from z=5 cm to z=6.6 cm, and also virtually (or mathematically) rotates the model representing the surface of the gantry 12 from 45° to 49°. FIG. 5C illustrates the models of FIG. 5B, particularly showing the models being virtually (mathematically) moved in accordance with a treatment plan to simulate an execution of the treatment plan. As the collision prediction mechanism 150 moves one or more of the models virtually, the collision prediction mechanism 150 determines whether a surface of one of the models touches, intercepts, or comes into a prescribed proximity with, a surface of another one of the models. If so, the collision prediction mechanism 150 then determines that there is a possible collision between the corresponding objects. Otherwise, the collision prediction mechanism 150 may determine that there is no possible collision, and the treatment procedure may proceed forward. In some cases, the collision prediction mechanism 150 may be configured for generating an output to indicate the possible collision or an absence of the possible collision.

In some embodiments, the processing unit 140 or another processing unit may be configured to provide one or more recommendations on how to modify the treatment plan based on the collision data and a dosage requirement of the treatment plan. For example, the processing unit 140 may be configured to determine one or more alternative treatment plans that address the potential collision issue while meeting the dosage requirement. In such cases, a user may select one of the recommendations (e.g., one of the proposed alternative treatment plans) for treating a patient. In other embodiments, the processing unit 140 or another processing unit may be configured to automatically modify the treatment plan in order to accomplish the dosage requirement and to avoid collision.

In the illustrated embodiments, the model representing the surface of the patient 20 is positionally slaved to the model representing the patient support 14, so that virtual movement of the model representing the patient support 14 will also cause the model representing the surface of the patient 20 to move correspondingly. In one implementation, the model representing the surface of the patient 20 is coupled to the model of the patient support 14, so that the model of the surface of the patient 20 and the model of the patient support 14 can be virtually positioned (e.g., translated and/or rotated) as a single unit. In another technique, the model including the surface profile of the patient 20 may also include a surface profile of the patient support 14, so that a virtual movement of the model will move both the surface model of the patient 20 and the surface model of the patient support 14.

In some embodiments, the collision prediction mechanism 150 may be configured to receive the treatment plan electronically, and process the trajectories prescribed in the treatment plan, so that information from the treatment plan can be extracted for use by the collision prediction mechanism 150 to mathematically simulate movements of the objects involved in the treatment procedure. For example, the collision prediction mechanism 150 may convert trajectories of the treatment components (e.g., gantry 12, patient support 14, imager 80, kV imager, collimator, etc.) prescribed by the treatment plan to a format or a set of positional parameters that can be used by the collision prediction mechanism 150 to simulate movements of the objects involved in the treatment procedure (e.g., components of the treatment system 10 and the patient 20).

In some embodiments, when the processing unit 140 determines that there is a possible collision that may happen if the treatment is allowed to go forward, the processing unit 140 may generate a signal to prevent the treatment system 10 from being operated to execute the treatment plan, may generate a visual signal, may generate an audio warning signal, or a combination of the above.

In some embodiments, a patient position monitoring system may be provided for monitoring a position of the patient 20 during a treatment procedure. For example, one or more optical camera(s) may be provided for viewing the patient during a treatment procedure. Images from the camera(s) may be analyzed by a processing unit (e.g., the processing unit 140 or another processing unit) to determine if certain parts (e.g., head, arms, legs, etc.) of the patient 20 remain stationary during the treatment procedure. If it is determined that the patient 20 has moved out of a desired position during the treatment procedure, the processing unit may stop the treatment procedure. Also, in the illustrated embodiments, after the treatment procedure is stopped, the collision prediction technique described above may be performed again to check for possible collision before the treatment procedure is resumed. In some embodiments, the processing unit 140 may automatically perform the collision prediction in response to a detected unwanted movement of the patient 20. In other embodiments, the collision prediction system 100 may provide a user interface (e.g., a one-click mechanism, such as a button) that allows the user to launch the virtual treatment process to get an immediate assessment of whether the treatment plan in question is collision-free based on the new patient position. In particular, because the patient 20 has moved, the surface profile of the patient 20 has also changed. When the collision prediction is performed in response to the patient's movement, the depth cameras 130 generate depth images that will capture the new surface profile of the patient. The processing unit 140 of the collision prediction system 100 then creates a new model that represents the new surface profile of the patient 20, and virtually executes the rest of the treatment plan to simulate the rest of the treatment procedure to determine if there is any possible collision between the patient and any of the components of the treatment system 10 based on the new patient position. If there is no possible collision, then the treatment may proceed.

Figure 6:
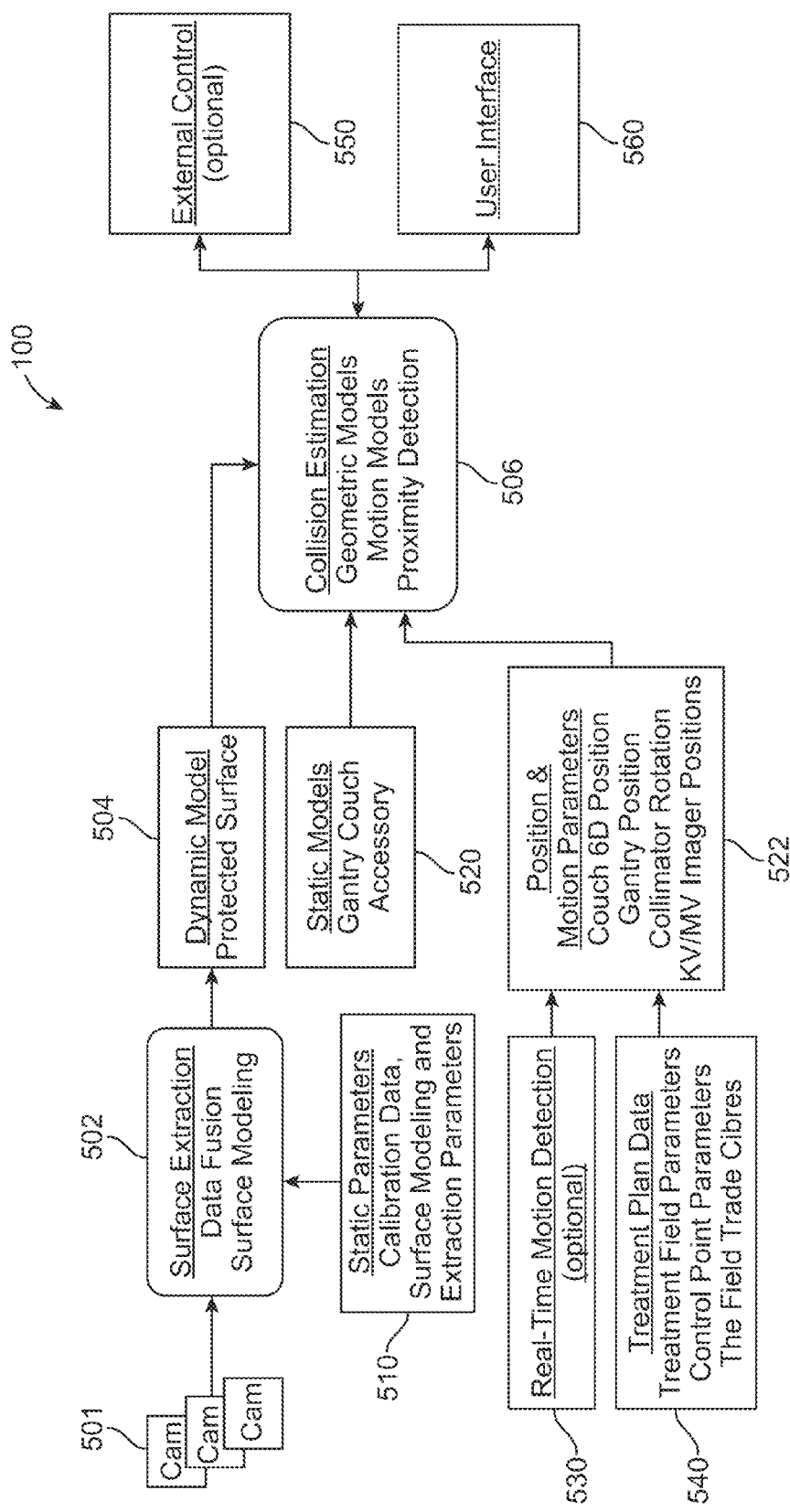
FIG. 6 illustrates an implementation of the system of FIG. 2.

FIG. 6 illustrates an implementation of the collision prediction system 100. The collision prediction system 100 is configured to process images 501 from camera(s) 130. The collision prediction system 100 includes a surface extraction module 502 configured to extract surfaces from the image(s). The surface extraction module 502 may also be configured to perform data fusion and/or surface modeling. Also, in some cases, static parameters may be provided for the surface extraction module 502 to perform its function. For example, as shown in item 510 in the figure, calibration data, surface modeling parameter(s), surface extraction parameter(s), or any combination of the foregoing, may be input to the surface extraction module 502.

The collision prediction system 100 also includes a dynamic model module 504 configured to determine a protected surface. In some embodiments, the protected surface may be represented by a model modeling a surface of the patient.

The collision prediction system 100 also includes a static model module 520 configured to determine models of different components involved in the treatment procedure. For example, the static model module 520 may be configured to determine models representing surfaces of the gantry 12, the patient support 14, and other components.

The collision prediction system 100 also includes a position and motion parameters module 522 configured to determine the positions of the various components (e.g., patient support 14, gantry 12, collimator, imager 80, kV imager, etc.). In some cases, the position and motion parameters module 522 may include a communication interface for providing communication between the treatment system 10 and the collision prediction system 100, so that the positions of the various components of the treatment system 10 may be communicated from the treatment system 10 to the collision prediction system 100. The position and motion parameters module 522 is configured to pass these information to a collision prediction mechanism 506 for processing.

The position and motion parameters module 522 is also configured to receive treatment plan information 540, and extract information from the treatment plan for later use by the collision prediction system 100. The extracted information may include prescribed positions of the various components at different stages of the treatment procedure. For example, the extracted information may indicate that the gantry 12 is to be rotated clockwise from 40° to 46° at certain stage of the treatment, and that the patient support 14 is to be translated in a Z-direction from coordinate of 35 to coordinate of 60, etc.

The collision prediction system 100 also includes a collision prediction mechanism 506 (which may be the collision prediction mechanism 150 described previously) configured to place the models into a coordinate frame based on input from the position parameters module 522, so that their respective positions match those in the real-world setup. The collision prediction mechanism 506 is also configured to virtually execute a treatment plan by virtually (mathematically) moving one or more of the models based on the extracted treatment plan information to simulate movement(s) of the respective object(s) prescribed by the treatment plan. In some cases, the collision prediction mechanism 506 is configured to consider motion models for the respective components when virtually moves the models representing the surfaces of the various objects. The motion models indicate direction and degree of movements for the different respective object surface models. Also, in some cases, the models representing the surfaces of the objects themselves may include respective positional information that corresponds with the real-world setup. Furthermore, in some cases, the models representing the surfaces of the objects themselves may include information regarding degree and direction(s) of movement(s).

As shown in the figure, the collision prediction system 100 also optionally includes a motion detection module 530 configured to detect a movement of the patient 20. In some embodiments, the motion detection module 530 may be configured to receive optical images from an optical camera, and process those images to determine if there is any patient motion during an actual treatment procedure. For example, the motion detection module 530 may subtract a current image from a reference image (obtained during a patient setup). If there has been no patient motion, the resulting subtracted image will have pixel values being zero or being close to zero. If there has been patient motion, the resulting subtracted image will have pixel values that are significantly different from zero.

In the illustrated embodiments, if the motion detection module 530 detects a patient movement, then the collision prediction system 100 generates a signal to stop an operation of the treatment system 10 so that the treatment procedure may be paused. The collision prediction system 100 then obtains image(s) from the camera(s) 130, and the surface extraction module 602 and the dynamic model 604 then process the image(s) to update the model representing the surface of the patient 20. Also, the position parameters module 522 determines the positions of the various components (e.g., patient support 14, gantry 12, collimator, imager 80, kV imager, etc.). The updated model of the patient and the position information regarding the positions of the components are then passed to the collision prediction mechanism 506. The collision prediction mechanism 506 then place the models of the components so that they match up with the real-world set up, and then virtually executes the rest of the treatment plan by virtually (mathematically) moving one or more of the models to simulate movement(s) of the respective object(s) prescribed by the rest of the treatment plan that has not yet been performed, in order to determine whether there is any possible collision between components of the treatment system 10 or between one or more components and the patient 20.

As shown in FIG. 6, the collision prediction system 100 also includes a user interface 560. The user interface 560 may include any user input device, such as a keyboard, a mouse, a touch pad, a button, a knob, etc., for allowing a user to enter input to the collision prediction system 100. The user input may be one or more input for identifying surfaces of different objects (e.g., patient, patient support 14, gantry 12, imager 80, kV imager, etc.) involved in the treatment procedure. The user input may also include information regarding positions of the components in the treatment system 10, and/or degrees and directions of movements for the various components. In some embodiments, the user input may be an input to stop a treatment procedure. In further embodiments, the user input may be a command to re-profile the patient. In such cases, when the collision prediction system 100 receives the input, that the camera(s) 130 will generate image(s) and the collision prediction system 100 will generate a new model representing a surface of the patient. The collision prediction system 100 will also determine the positions of the various components in response to such user input, and will automatically execute the treatment plan (or a remaining part of a treatment plan) virtually in order to simulate an execution of the treatment plan.

In some embodiments, the user interface 560 may also include a screen for displaying information to a user. For example, the user interface 560 may provide graphics indicating the model of the patient, and models of the various components in the treatment system 10. The user interface 560 may also display the models in relative position with respect to each other after they have been positioned to match up with the real-world setup. In addition, the user interface 560 may display an actual optical image of the system 10 with the patient 20. Such display may be in a side-by-side configuration with respect to a graphical image showing the models. Furthermore, the user interface 560 may display a processor-generated video showing a virtual movement of the model(s) as the treatment plan is virtually executed to simulate an actual treatment procedure. Also, the user interface 560 may provide results from the treatment simulation that is performed virtually by the collision prediction mechanism 506. For example, the results may indicate how close the components are relative to each other during the treatment simulation, whether any of the components touches or comes within a prescribed margin from another component, whether any of the components touches or comes within a prescribed margin from the surface of the patient, or any combination of the foregoing.

As shown in FIG. 6, the collision prediction system 100 also optionally includes an external control 550. The external control 550 may be any controller that is configured to use collision estimates. For example, the external control 550 may be a digital electronic controller that controls the motor moving the gantry of the radiation system. In such cases, the controller may automatically slow or stop the gantry based on output of the collision prediction algorithm. For example, the gantry may be automatically slowed as it approaches a collision surface, and may be automatically stopped before a collision occurs. It should be noted that the external control 550 is optional, and the collision prediction system 100 may or may not include such control.

Figure 7:
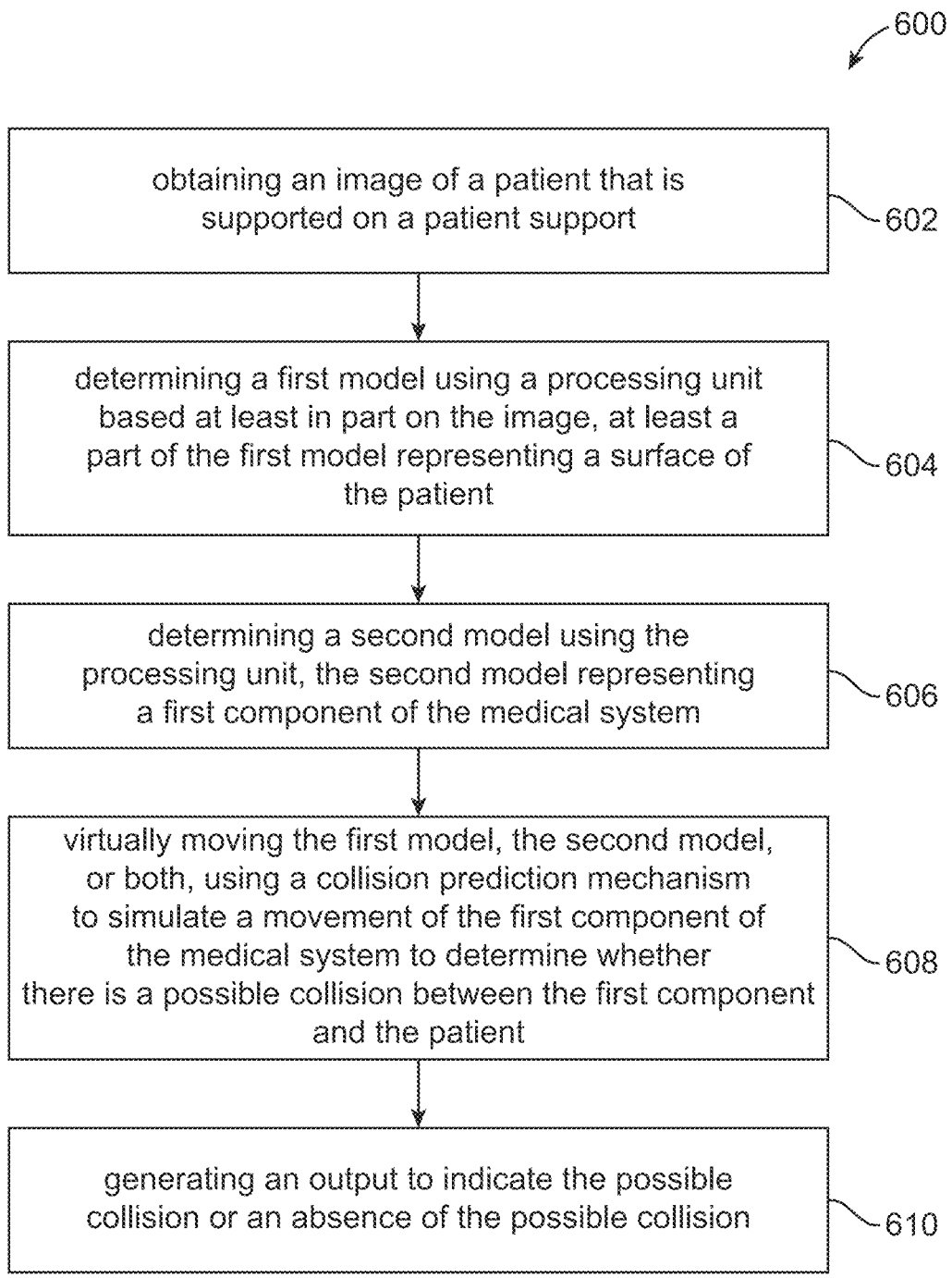
FIG. 7 illustrates a method for determining whether there is a possible collision between a patient and an object.

FIG. 7 illustrates a method 600 of detecting a possible collision in a medical procedure that involves a medical system. The method 600 includes obtaining an image of a patient that is supported on a patient support (item 602); determining a first model using a processing unit based at least in part on the image, at least a part of the first model representing a surface of the patient (item 604); determining a second model using the processing unit, the second model representing a first component of the medical system (item 606); virtually moving the first model, the second model, or both, using a collision prediction mechanism to simulate a movement of the first component of the medical system to determine whether there is a possible collision between the first component and the patient (item 608); and generating an output to indicate the possible collision or an absence of the possible collision (item 610).

In some cases, the method 600 further includes determining a third model representing the patient support.

In some cases, the method 600 further includes virtually moving the first model and the third model as a single unit.

In some cases, the first model includes a modeling of at least a part of the patient support 14.

In some cases, the method 600 further includes virtually moving the first model to simulate a movement of the patient due to a movement of the patient support 14.

In some cases, the act of determining the first model is performed in response to a movement of the patient.

In some cases, the act of determining the first model is performed after the patient is set up for a treatment procedure.

In some cases, the act of determining the first model is performed in response to a user entering a user input via a user interface.

In some cases, the method 600 further includes displaying a graphic indicating a movement trajectory of the second model.

In some cases, the method 600 further includes displaying a video indicating the virtual movement of the second model.

In some cases, the image comprises a depth image of the patient, and wherein the act of determining the first model comprises: identifying a portion in the depth image that corresponds with the surface of the patient; and using the identified portion in the depth image to create the first model.

In some cases, the act of determining the first model further comprises: identifying a portion in another depth image that corresponds with another surface of the patient; and combining the portion from the depth image and the portion in the other depth image.

In some cases, the act of determining the first model further comprises extracting a first set of points from the identified portion in the depth image.

In some cases, the act of determining the first model further comprises: identifying a portion in another depth image that corresponds with another surface of the patient; extracting a second set of points from the identified portion in the other depth image; and determining a third set of points representing a protected surface associated with the patient using the first set of points and the second set of points.

In some cases, the third set of points includes at least some of the first set of points, and at least some of the second set of points.

In some cases, the protected surface represented by the third set of points is away from the surface of the patient, and wherein the third set of points are away from at least some of the first set of points, and are away from at least some of the second set of points.

In some cases, the act of determining the first model further comprises determining a protected surface that is away from the surface of the patient.

In some cases, the medical system comprises a radiation treatment system.

In some cases, the first component comprises a gantry, a radiation source, a portal imager, or a kV imager.

In some cases, the image comprises a depth image, and wherein the method 600 further comprises removing stray points from the depth image.

In some cases, the act of virtually moving the second model is performed by executing a treatment plan virtually.

In some cases, the method 600 further includes: detecting a motion of the patient; and after the motion is detected, determining a position of the first component of the medical system.

In some cases, the act of virtually moving the second model is performed after the position of the first component of the medical system is determined.

In some cases, the method 600 further includes: determining a third model representing a second component of the medical system; and virtually moving the third model to simulate a movement of the second component.

In some cases, the collision prediction mechanism is a part of the processing unit.

In the above embodiments, the collision prediction system 100 is configured to automatically detect a possible collision. In other embodiments, a user may also participate in determining whether there is a possible collision. For example, in some cases, the monitor 56 may be used to display graphics (e.g., image, video, etc) showing the objects being virtually moved by the collision prediction mechanism 150, so that a user may identify a possible collision.

In some embodiments, the depth sensing camera 130 may have the ability to acquire optical images (e.g., infrared or visible images), simultaneously in addition to depth images. In other embodiments, there may be two separate cameras, one capturing depth images and the other capturing optical images. If depth and optical images are both acquired during the procedure, the processing unit 140 may display both images next to each other on the monitor 56, or superimpose the two images on top of each other, to show how the depth image corresponds with the optical image. Also, in some embodiments, the processing unit 140 may perform analysis using optical images to identify surfaces for the various objects involved in the treatment process. In one or more embodiments, the depth image and the optical image may be superimposed/overlaid to obtain a composite image that shows both depth and visible image.

In addition, in other embodiments, the cameras 130 may be any time-of-flight (TOF) cameras, such as those that use infrared, ultrasound, etc. In further embodiments, the cameras 130 may be configured to use structured light to generate images. Also, in other embodiments, the cameras 130 may be stereoscopic imaging devices.

Also, in other embodiments, the cameras 130 do not need to be depth cameras, and may be optical cameras. In such cases, surfaces of the various objects (e.g., patient 20, gantry 12, patient support 14, imager 80, kV imager, etc.) may be derived by processing the optical images obtained from two or more optical cameras that are positioned to view the treatment system 10 and the patient 20 from different angles.

Furthermore, it should be noted that the cameras 130 do not need to be mounted to a stationary object, and may instead be mounted on moving object(s). For example, the cameras 130 may be mounted to a moving gantry, or to a patient support.

In the above embodiments, the system and method have been described with reference to performing a virtual dry run of a treatment plan based on images from the camera(s) 130. In other embodiments, one or more features and/or techniques described herein may be applied for real time monitoring for collision avoidance. For example, in some embodiments, the processing unit 140 may be configured to analyze image(s) from the camera(s) 130, and determine whether any portion of the system comes too close (e.g., exceeds a threshold safety distance value) to the patient or to another portion of the system. If so, the processing unit 140 may generate a control signal to stop the treatment procedure. In some cases, the processing unit 140 may also be configured to modify the treatment plan or provide suggestions for allowing a user to modify the treatment plan.

Although the above embodiments have been described with reference to avoiding collision in a radiation treatment system, in other embodiments, the collision prediction system and technique described herein may be used with other types of medical devices. For example, in other embodiments, the collision prediction system and technique described herein may be used with a non-radiation treatment machine, such as an ultrasound treatment machine, a RF medical device, etc. Also, in other embodiments, the collision prediction system and technique described herein may be used with a non-treatment machine, such as an imaging device (e.g., a CT machine, a x-ray, a fluoroscopic machine, etc.).

Furthermore, in some embodiments, features described herein may be employed with other tools for management of treatment strategy and/or for determining a treatment plan. For example, the collision prediction feature described herein may be used together with another tool that assists management of treatment strategy based on probability density function(s), so that together they provide a more comprehensive tool for allowing management of treatment strategy and/or for determining a treatment plan. Systems and techniques for management of treatment strategy and for determining treatment plan based on probability density function(s) are described in U.S. patent application Ser. No. 13/960,642, filed on Aug. 6, 2013, the entire disclosure of the above application is expressly incorporated by reference herein. Also, the above referenced application discloses using probability density functions to represent different uncertainties associated with a treatment. Similar techniques may also be employed in the collision prediction algorithm to determine probability of two surface models colliding based on trajectory of each object's movement.

Specialized Processing System

Figure 8:
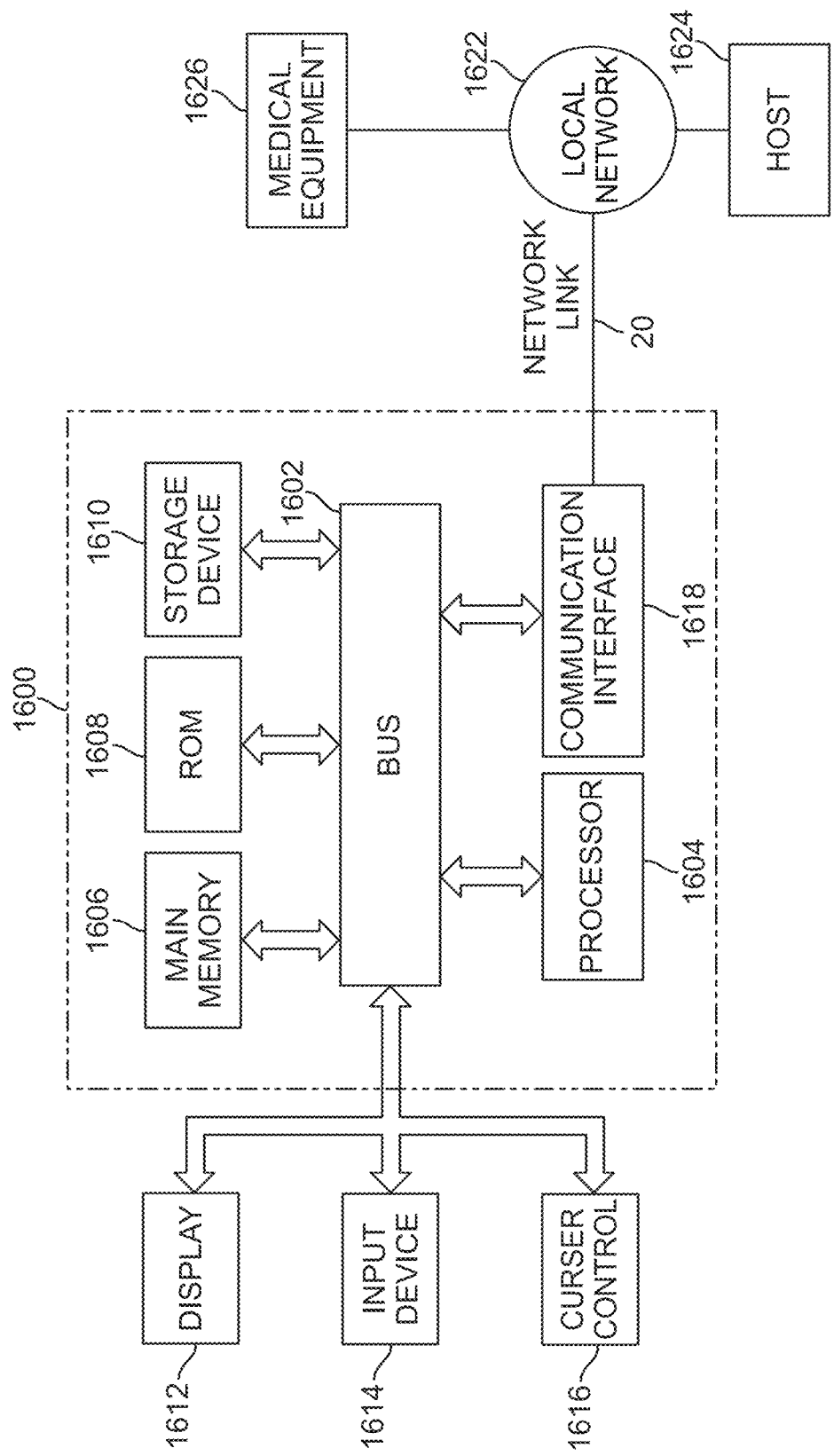
FIG. 8 illustrates a computer system with which embodiments described herein may be implemented.

FIG. 8 is a block diagram illustrating an embodiment of a specialized processing system 1600 that can be used to implement various embodiments described herein. For example, the processing system 1600 may be configured to implement the method of FIG. 7 in accordance with some embodiments. Also, in some embodiments, the processing system 1600 may be used to implement the processing unit 140 of FIG. 2 and/or the processing unit 54 of FIG. 1. Processing system 1600 includes a bus 1602 or other communication mechanism for communicating information, and a processor 1604 coupled with the bus 1602 for processing information. The processor 1604 may be an example of the processor 54 of FIG. 1A, an example of the processor 80 of FIG. 1B/1C, or an example of any processor described herein. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An apparatus for detecting a possible collision in a medical procedure, comprising:
   a camera for providing an image of a patient that is supported on a patient support; and
   a processing unit configured for:
      determining a first model based at least in part on the image, at least a part of the first model corresponding with a surface of the patient, and
      determining a second model, the second model representing a first component of the medical system; and
   a collision prediction mechanism configured for virtually moving the first model, the second model, or both, to simulate a movement of the first component of the medical system to determine whether there is a possible collision between the first component and the patient;
   wherein the collision prediction mechanism is also configured for generating an output to indicate the possible collision or an absence of the possible collision; and
   wherein the processing unit is configured for determining the first model in response to a movement of the patient.

2. An apparatus for detecting a possible collision in a medical procedure, comprising:
   a camera for providing an image of a patient that is supported on a patient support; and a processing unit configured for:
  determining a first model based at least in part on the image, at least a part of the first model corresponding with a surface of the patient, and
  determining a second model, the second model representing a first component of the medical system; and
a collision prediction mechanism configured for virtually moving the first model, the second model, or both, to simulate a movement of the first component of the medical system to determine whether there is a possible collision between the first component and the patient;
wherein the collision prediction mechanism is also configured for generating an output to indicate the possible collision or an absence of the possible collision; and
wherein the apparatus further includes a graphical output interface for providing a graphic indicating a movement trajectory of the second model.

3. An apparatus for detecting a possible collision in a medical procedure, comprising:
a camera for providing an image of a patient that is supported on a patient support; and
a processing unit configured for:
  determining a first model based at least in part on the image, at least a part of the first model corresponding with a surface of the patient, and
  determining a second model, the second model representing a first component of the medical system; and
a collision prediction mechanism configured for virtually moving the first model, the second model, or both, to simulate a movement of the first component of the medical system to determine whether there is a possible collision between the first component and the patient;
wherein the collision prediction mechanism is also configured for generating an output to indicate the possible collision or an absence of the possible collision; and
wherein the apparatus further includes a graphical output interface for providing a video indicating the virtual movement of the second model.

4. An apparatus for detecting a possible collision in a medical procedure, comprising:
a camera for providing an image of a patient that is supported on a patient support; and
a processing unit configured for:
  determining a first model based at least in part on the image, at least a part of the first model corresponding with a surface of the patient, and
  determining a second model, the second model representing a first component of the medical system; and
a collision prediction mechanism configured for virtually moving the first model, the second model, or both, to simulate a movement of the first component of the medical system to determine whether there is a possible collision between the first component and the patient;
wherein the collision prediction mechanism is also configured for generating an output to indicate the possible collision or an absence of the possible collision; and
wherein the image comprises a depth image of the patient, and wherein the processing unit is configured for, in a process to determine the first model:
  identifying a portion in the depth image that corresponds with the surface of the patient; and
  using the identified portion in the depth image to create the first model.

5. The apparatus of claim 4, wherein the processing unit is also configured for determining a third model representing the patient support.

6. The apparatus of claim 5, wherein the collision prediction mechanism is further configured for virtually moving the first model and the third model as a single unit.

7. The apparatus of claim 4, wherein the first model includes a modeling of at least a part of the patient support.

8. The apparatus of claim 7, wherein the collision prediction mechanism is further configured for virtually moving the first model to simulate a movement of the patient due to a movement of the patient support.

9. The apparatus of claim 4, wherein the processing unit is configured for determining the first model after the patient is set up for a treatment procedure.

10. The apparatus of claim 4, wherein the processing unit is configured for determining the first model in response to a user entering a user input via a user interface.

11. The apparatus of claim 4, wherein the processing unit is configured for, in a process to determine the first model:
  identifying a portion in another depth image that corresponds with another surface of the patient; and
  combining the portion from the depth image and the portion in the other depth image.

12. The apparatus of claim 4, wherein the processing unit is configured for extracting a first set of points from the identified portion in the depth image.

13. The apparatus of claim 12, wherein the processing unit is configured for, in a process to determine the first model:
  identifying a portion in another depth image that corresponds with another surface of the patient;
  extracting a second set of points from the identified portion in the other depth image; and
  determining a third set of points representing a protected surface associated with the patient using the first set of points and the second set of points.

14. The apparatus of claim 13, wherein the third set of points includes at least some of the first set of points, and at least some of the second set of points.

15. The apparatus of claim 13, wherein the protected surface represented by the third set of points is away from the surface of the patient, and wherein the third set of points are away from at least some of the first set of points, and are away from at least some of the second set of points.

16. The apparatus of claim 4, wherein the processing unit is configured for, in a process to determine the first model, determining a protected surface that is away from the surface of the patient.

17. The apparatus of claim 4, wherein the medical system comprises a radiation treatment system.

18. The apparatus of claim 17, wherein the first component comprises a gantry, a radiation source, a portal imager, or a kV imager.

19. The apparatus of claim 4, wherein the processing unit is further configured for:
  determining a third model representing a second component of the medical system; and
  virtually moving the third model to simulate a movement of the second component.

20. The apparatus of claim 4, wherein the collision prediction mechanism is a part of the processing unit.

21. The apparatus of claim 4, wherein the camera is configured to generate the image based on time-of-flight technique, stereoscopic technique, structured light, or ultrasound.

22. The apparatus of claim 21, further comprising an optical device for providing infrared illumination or pattern projection for enhancing the stereoscopic technique.

23. The apparatus of claim 4, further comprising an additional camera.

24. An apparatus for detecting a possible collision in a medical procedure, comprising:
a camera for providing an image of a patient that is supported on a patient support; and
a processing unit configured for:
determining a first model based at least in part on the image, at least a part of the first model corresponding with a surface of the patient, and
determining a second model, the second model representing a first component of the medical system; and
a collision prediction mechanism configured for virtually moving the first model, the second model, or both, to simulate a movement of the first component of the medical system to determine whether there is a possible collision between the first component and the patient;
wherein the collision prediction mechanism is also configured for generating an output to indicate the possible collision or an absence of the possible collision; and
wherein the image comprises a depth image, and wherein the processing unit is further configured for removing stray points from the depth image.

25. The apparatus of claim 24, wherein the collision prediction mechanism is configured for virtually moving the second model by executing a treatment plan virtually.

26. An apparatus for detecting a possible collision in a medical procedure, comprising:
a camera for providing an image of a patient that is supported on a patient support; and
a processing unit configured for:
determining a first model based at least in part on the image, at least a part of the first model corresponding with a surface of the patient, and
determining a second model, the second model representing a first component of the medical system; and
a collision prediction mechanism configured for virtually moving the first model, the second model, or both, to simulate a movement of the first component of the medical system to determine whether there is a possible collision between the first component and the patient;
wherein the collision prediction mechanism is also configured for generating an output to indicate the possible collision or an absence of the possible collision;
wherein the apparatus further includes a motion detection device configured to detect a motion of the patient; and
wherein the collision prediction mechanism is configured to, after the motion is detected, determine a position of the first component of the medical system.

27. The apparatus of claim 26, wherein the collision prediction mechanism is configured for virtually moving the second model after the position of the first component of the medical system is determined.

28. An apparatus for detecting a possible collision in a medical procedure, comprising:
a camera for providing an image of a patient that is supported on a patient support; and
a processing unit configured for:
determining a first model based at least in part on the image, at least a part of the first model corresponding with a surface of the patient, and
determining a second model, the second model representing a first component of the medical system; and
a collision prediction mechanism configured for virtually moving the first model, the second model, or both, to simulate a movement of the first component of the medical system to determine whether there is a possible collision between the first component and the patient;
wherein the collision prediction mechanism is also configured for generating an output to indicate the possible collision or an absence of the possible collision; and
wherein the camera is configured to generate the image using ultrasound.

29. An apparatus for detecting a possible collision in a medical procedure, comprising:
a camera for providing an image of a patient that is supported on a patient support; and
a processing unit configured for:
determining a first model based at least in part on the image, at least a part of the first model corresponding with a surface of the patient, and
determining a second model, the second model representing a first component of the medical system; and
a collision prediction mechanism configured for virtually moving the first model, the second model, or both, to simulate a movement of the first component of the medical system to determine whether there is a possible collision between the first component and the patient;
wherein the collision prediction mechanism is also configured for generating an output to indicate the possible collision or an absence of the possible collision; and
wherein the image comprises a depth image, and wherein the processing unit is configured to obtain a visible image of the patient.

30. The apparatus of claim 29, wherein the processing unit is configured to output both the visible image and the depth image for display on a screen.

31. A method of detecting a possible collision in a medical procedure that involves a medical system, comprising:
obtaining an image of a patient that is supported on a patient support;
determining a first model using a processing unit based at least in part on the image, at least a part of the first model corresponding with a surface of the patient;
determining a second model using the processing unit, the second model representing a first component of the medical system;
virtually moving the first model, the second model, or both, using a collision prediction mechanism to simulate a movement of the first component of the medical system to determine whether there is a possible collision between the first component and the patient; and
generating an output to indicate the possible collision or an absence of the possible collision;
wherein the image comprises a depth image of the patient, and wherein the first model is determined by:
identifying a portion in the depth image that corresponds with the surface of the patient; and
using the identified portion in the depth image to create the first model.

32. A product having a non-transitory medium storing a set of instructions, an execution of which by a processing unit causes a method for detecting a possible collision in a medical procedure to be performed, the method comprising:
obtaining an image of a patient that is supported on a patient support;
determining a first model using the processing unit based at least in part on the image, at least a part of the first model corresponding with a surface of the patient;
determining a second model using the processing unit, the second model representing a first component of a medical system;
virtually moving the first model, the second model, or both, using a collision prediction mechanism to simulate a movement of the first component of the medical system to determine whether there is a possible collision between the first component and the patient; and
generating an output to indicate the possible collision or an absence of the possible collision;
wherein the image comprises a depth image of the patient, and wherein the first model is determined by:
identifying a portion in the depth image that corresponds with the surface of the patient; and
using the identified portion in the depth image to create the first model.

* * * * *